United States Patent [19]

Tibes et al.

[11] Patent Number: 4,778,799

[45] Date of Patent: Oct. 18, 1988

[54] SYNERGISTIC COMBINATION OF FLUPIRTIN AND NON-STEROIDAL ANTIPHLOGISTIC

[76] Inventors: Ulrich Tibes, Am Sandberg 102, D-6000 Frankfurt am Main 70; Carl H. Weischer, Schmidtbonnstrasse 8, D-5300 Bonn 1; Helmut Hettche, Buchrainweg 65, D-6050 Offenbach am Main; Hans-Peter Breuel, Am Jungstuck 34, D-6500 Mainz 43, all of Fed. Rep. of Germany

[21] Appl. No.: 102,240

[22] Filed: Sep. 28, 1987

Related U.S. Application Data

[63] Continuation of Ser. No. 821,818, Jan. 23, 1986, abandoned.

[30] Foreign Application Priority Data

Jan. 23, 1985 [DE] Fed. Rep. of Germany ....... 3502005

[51] Int. Cl.$^4$ .................... A61K 31/19; A61K 31/435

[52] U.S. Cl. .................... 514/277; 514/557
[58] Field of Search .................. 514/557, 277

[56] References Cited

U.S. PATENT DOCUMENTS 4,554,281 11/1985 von Bebenburg .................. 514/353

OTHER PUBLICATIONS

Deutsche Apotheker Zeitung, 124th Year, No. 25, Jun. 21, 1984, pp. 33–44.
Chem. Abst. vol. 95, p. 632.
Arzneimittel Forschung, Drug Research, vol. 35 (1), No. 1, Jan. 1985, pp. 30–43.

*Primary Examiner*—Stanley J. Friedman
*Attorney, Agent, or Firm*—Cushman, Darby & Cushman

[57] ABSTRACT

Medicines are prepared having a synergistic effect containing a combination of the analgesic Flupirtin and at least one non-steroidal antiphlogistic.

18 Claims, No Drawings

SYNERGISTIC COMBINATION OF FLUPIRTIN AND NON-STEROIDAL ANTIPHLOGISTIC

This application is a continuation of Ser. No. 821,818, filed Jan. 23, 1986, now abandoned.

BACKGROUND OF THE INVENTION

Flupirtin is a medicine having analgetic properties. Its chemical name is 2-amino-3-carbethoxyamino-6-(fluoro-benzylamino)-pyridine having the following structural formula:

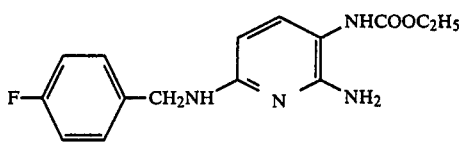

Flupirtin and its salts with physiologically unobjectionable acids have an outstanding analgetic main activity as well as a slight antiphlogistic action. It has now been found that the action of Flupirtin and its salts suprisingly is synergistically increased through combination with non-steroidal antiphlogistics, whereby simultaneously the activity of the antiphlogistic likewise experiences a synergistic increase. The active materials of the combination of the invention thus potentiate each other in their action.

The problem of the invention is to prepare improved medicines having analgetic and antiphlogistic action.

SUMMARY OF THE INVENTION

There is provided a medicine containing as active material flupirtin and at least one non-steroidal antiphlogistic or a salt of these compounds with physiologically unobjectionalbe acids or physiologically non-toxic metals. The non-steroidal antiphlogistic can be acetylsalicylic acid, an arylacetic acid, e.g. phenylacetic acid, an arylpropionic acid, e.g. phenylpropionic acid, or an oxicam. Each dosage unit of the combination can have 10 to 1900 mg, preferably 15–1500 mg of Flupirtin and 1 to 1600 mg of the non-steroidal antiphlogistic. More specifically the combination can contain 10 to 1200 mg, preferably 15 to 900 of Flupirtin and 2 to 500 mg of the antiphlogistic. Still more specifically the combination can contain 50 to 600 mg, preferably 50 to 400 mg of Flupirtin and 5 to 300 mg of the antiphlogistic. Per part of the Flupirtin the combination can contain 0.05 to 120, preferably 0.05 to 60 parts by weight of the non-steroidal antiphlogistic.

The parts by weight or amounts set forth above refer in each case to the pure active material, that is not to the salt of this active material.

The antiphlogistics which are used with the Flupirtin are non-steroidal antiphlogistics with outstanding antiphlogistic main activity and a lower analgetic side action component. Hereby it is a matter of antiphlogistics whose action depends on the checking of the formation of inflammation intermediates (materials which among others, relieve edemas), especially the formation of cyclooxygenase products. Such antiphlogistics includes acetylsalicylic acid, arylacetic acids, e.g. phenylacetic acids, or arylpropionic acids, e.g. phenylpropionic acid or Oxicames. For example, it is a matter of acetic acid derivatives which contains a substituted aromatic group in the alpha-position. Among these aromatic groups, especially there are included a phenyl group, an indole group, an indane group, an indene group, a pyrrole group, a thiazole group, a pyrazole group, a xanthene group, a thioxanthene group or a 1,3,4-trihydropyrano[3,4,b]-indole group. Examples of such non-steroidal antiphlogistics are Indometacin, Glucametacin, Sulindac, Zomepirac, Diclofenac, Tolmetin, Amfenac, Fentiazac, Etodolac, Furofenac, Insofezolac, Isoxepac, Tiopinac, Pirazolac. Especially advantageous is a combination of Flupirtin with Diclofenac. Likewise, it is a matter for example of propionic acid derivatives which also contain in the alpha or beta-position a substituted aromatic group, whereby as aromatic group there is used a phenyl group, a phenylcarbonyl group, a biphenyl group, naphthyl group, indole group, 3H-3-oxaindole group, thiophene group, carbazole, oxazole group or a furane group. Examples of these are Flurbiprofen, Fenoprofen, Ketoprofen, Naproxen, Benoxaprofen, Pirprofen, Indoprofen, Carprofen, Tiaprofenic acid, Suprofen, Oxaprozin, Orpanoxin, Fenbufen. Furthermore, there can be used as non-steroidal antiphlogistics Oxicames (benzothienothiazine-3-carboxylic acid amides) which are substituted on the carboxamide group for example by a pyridyl group or a 5-methyl-isoxazolyl group. Examples of these are Piroxicam, Isoxicam, Tenoxicam.

Especially it is a matter of antiphlogistics which are arylcarboxylic acids such as arylacetic acids or arylpropionic acids of the formula:

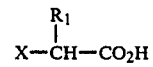

and their salts with physiologically unobjectionable metals (cations) or acids whereby in formula I R₁ is hydrogen, in case X is a 2-(2,6-dichlorophenylamino)-phenyl group, a 2-amino-3-phenylcarbonyl-phenyl group, an N-methyl-4-methyl-5-(4-chloro-phenylcarbonyl)-2-pyrrolyl-group, a N-methyl-5-(4-methylphenylcarbonyl)-2-pyrrolyl group, a 1-(4-chlorophenylcarbonyl)-2-methyl-5-methoxy-indolyl group, a 1-(4-methylsulfinyl-phenylmethylene)-2-methyl-5-fluoro-3-indenyl group, a 2-phenyl-4-(4-chlorophenyl)-5-thiazolyl group, a 1,3,4-triphenyl-5-pyrazolyl group, a 2-ethyl-5-indanyl group, a 1-(4-fluoro-phenyl)-4-(4-chloro-phenyl)-3-pyrazolyl group, a 9-oxo-2-xanthenyl group, a 9-oxo-3-thioxanthenyl group, a 1,8-diethyl-1,3,4-trihydropyrano[3,4-b]-1-indolyl group, a (4,5-diphenyl-2-oxazolyl)-methyl group, a (5-chlorophenyl-2-furyl)-hydroxymethyl group or a (4-cyclohexylphenyl)-carbonylmethyl group, whereby in the case of the 1-(4-chloro-phenylcarbonyl)-2-methyl-5-methoxy-3-indolyl group the carboxy group of compound I also can be present in the form of glucosamide and in case R₁ is methyl, in case X is a 2-fluoro-4-biphenyl group, a 3-phenoxy-phenyl group, a 3-phenylcarbonyl-phenyl group, a 6-methoxy-2-naphthyl group, a [3-chloro-4-(3-pyrrolino)-phenyl] group, a 4-(1-oxo-1,3-dihydro-isoindol-2-yl)-phenyl group, a 6-chloro-2-carbazolyl group, a 5-phenylcarbonyl-2-thienyl group, a 4-(2-thienylcarbonyl)-phenyl group or a 2-(4-chlorophenyl)-5-benzoxazolyl group, or whereby the structure part X—CH(R₁)— is the 2-acetoxy-phenyl group.

Furthermore, it is a matter according to the invention of the use of antiphlogistics which are oxicames (benzothiazin-3-carboxylic acid amides) of the formula:

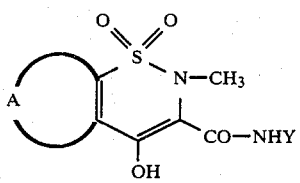

and optionally their salts with physiologically unobjectionable metals (cations) or acids, whereby A of formula II is a fused benzo group or a fused thieno-(2,3)-group and Y represents a 2-pyridyl group or a 5-methyl-3-isoxazolyl group.

Likewise according to the invention a combination of Flupirtin with acetylsalicylic acid results in medicines with surprising synergistic action.

Likewise there can be used as non-steroidal antiphlogistics for the combination of the invention fenamates such as for example Mefenamic acid, Flufenamic acid, Meclofenamic acid (for example also in the form of a salt, for example as the sodium salt).

The Flupirtin is preferably used as an acid addition salt, whereby especially the salts with hydrohalic acids (for example the hydrochloride and hydrobromide) or organic acids (for example the maleate or gluconate) are employed. The non-steroidal antiphlogistics are generally not used in the form of their salts. In case they are employed as salts they are used for examples as alkali salts (for example the sodium salt and the potassium salt).

The combination of the invention shows for example in the Randall-Selitto Test, in the Acetic Acid-Writhing Test or in the Hot-Plate Test a synergism of the analgetic action, which compared to the analgesy of pure Flupirtin (the Flupirtin was always used as the maleate, gluconate or hydrochloride) and the analgetically active portion of the non-steroidal antiphlogistics is increased beyond the additive effect. It is surprising that both the analgetic main activity of Flupirtin and the analgetically active component of the non-steroidal analgetics are increased synergistically. Likewise it is surprising, moreover, that both the antiphlogistically weak side components of Flupirtin and the antiphlogistic main activity of the non=steroidal antiphlogistics are increased (for example in the Carrageenin-Edema Test, Bradykinin-Edema test or Adjuvans-Arthritis test). Test on the mouse at a dosage of 2.6 mg/kg per os Flupirtin and 0.98 mg/kg per os of the antiphlogistic Diclofenac the analgetic effect of Flupirtin was increased around a factor of 17. The analgetic activity of the Diclofenac for example at a dosage of 2.24 mg/kg Flupirtin and 1.77 mg/kg Diclofenac was increased around a factor of 7. Thus for example, in the Acetic Acid-Writhing Test on the mouse the analgetically effective $ED_{50}$ of Flupirtin of 44 mg/kg per os is reduced to 2.6 mg/kg per os and the analgeticaly effective $ED_{50}$ of the Diclofenac is reduced from 12 to 1.8. mg/kg. (The values refer to the previously stated mixture.) Hereby there is held constant Diclofenac at 0.98 mg/kg per os and Flupirtin dispensed in the dosages 2.24; 3.57 and 9 mg/kg per os. In the other case Flupirtin is held constant at 2.24 mg/kg and Diclofenac from 0.49 mg/kg to 15.6 mg/kg per os, in each case increased around a factor of 2. What has been stated previously is also true for Indometacin, Glucametacin, Naproxen, Piroxicam, acetylsalicylic acid, Sulindac and Isoxicam. For the last mentioned antiphlogistics, the factors for the increase in activity of the analgetic action are for example between 2-15 compared to the analgetic side activity component of the pure antiphlogistic (Acetic-Writhing Test of the mouse).

The effect of the combination according to the invention can be seen from the following investigations. These investigations were carried out in the Acetic Acid Test (Writhing Test) on the white mouse. Hereby there were held constant both the Flupirtin dosage (gluconate or hydrochloride) and the dosage of the antiphlogistic (Diclofenac) varied and also the dosage of the antiphlogistic held constant and the dosage of Flupirtin changed and always there was determined in the first case the $ED_{50}$ of the analgetic component of the antiphlogistic and in the second case the analgetic main activity of the Flupirtin in the combination. (Method According to Forth, Henschler and Rummel, Lehrbuch Pharmakologie und Toxikologie, published 1980, page 65; Wissenschaftsverlag, Bibliographisches Institut Mannheim, Vienna and Zurich). The results are set forth in Table 1:

TABLE 1

Writhing According to Koster et al; Fed. Proc. 18, 412 (1959)
Animal: White Mouse (NMRI-Mouse); Application: per os

| Active Material Combination | Active Material Dosage (mg/kg) per oral | Activity in % Average of 10 Mice | $ED_{50}$ mg/kg Determination 30 Minutes After Giving the Substance. Method of Linear Regression |
|---|---|---|---|
| Flupirtin (Gluconate) alone | | | Flupirtin |
| | 0.56 | 19.2 | |
| | 1.12 | 28.0 | |
| | 2.24 | 37.6 | |
| | 4.47 | 46.4 | 43.9 |
| | 8.93 | 38.4 | |
| | 17.85 | 22.4 | |
| | 35.7 | 61.6 | |
| Diclofenac alone | | | Diclofenac |
| | 3.9 | 33.3 | |
| | 7.8 | 50.0 | |
| | 15.6 | 45.8 | 12.1 |
| | 31.25 | 66.0 | |
| | 62.5 | 67.4 | |
| | 125.0 | 91.7 | |
| 2.24 mg/kg Flupirtin Gluconate) + Diclofenac | Diclofenac | | Diclofenac in the Combination |
| | 0.49 | 31.5 | |

TABLE 1-continued

Writhing According to Koster et al; Fed. Proc. 18, 412 (1959)
Animal: White Mouse (NMRI-Mouse); Application: per os

| Active Material Combination | Active Material Dosage (mg/kg) per oral | Activity in % Average of 10 Mice | $ED_{50}$ mg/kg Determination 30 Minutes After Giving the Substance. Method of Linear Regression |
|---|---|---|---|
| | 0.98 | 43.4 | |
| | 1.95 | 51.7 | |
| | 3.9 | 55.2 | 1.77 |
| | 7.8 | 76.2 | |
| | 15.6 | 79.7 | |
| 3.57 mg/kg Flupirtin (Hydrochloride) + Diclofenac | | | Diclofenac in the Combination |
| | Diclofenac | | |
| | 0.13 | 30.8 | |
| | 0.25 | 35.9 | |
| | 0.49 | 53.2 | 0.56 |
| | 0.98 | 60.9 | |
| | 1.95 | 66.0 | |
| | 3.90 | 71.8 | |
| | 7.80 | 78.8 | |
| 9 mg/kg Flupirtin (Gluconate) + Diclofenac | | | Diclofenac in the Combination |
| | Diclofenac | | |
| | 0.13 | 41.9 | |
| | 0.25 | 47.3 | |
| | 0.49 | 56.1 | |
| | 0.98 | 62.8 | 0.29 |
| | 1.95 | 66.9 | |
| | 3.90 | 75.0 | |
| | 7.80 | 79.1 | |
| 0.98 mg/kg Diclofenac + Flupirtin (Gluconate or Hydrochloride) | | | Flupirtin in the Combination |
| | Flupirtin | | |
| | 2.24 | 43.4 | |
| | 3.57 | 60.9 | 2.6 |
| | 9.0 | 62.8 | |
| 0.49 mg/kg Diclofenac + Flupirtin (Gluconate or Hydrochloride) | | | Flupirtin in the Combination |
| | Flupirtin | | |
| | 2.24 | 31.5 | |
| | 3.57 | 53.2 | |
| | 9.00 | 56.1 | 5.1 |

Thus it can be seen from Table 1 there is a synergistic effect in the analgetic effect of the combination, namely both in regard to the Flupirtin and also the analgetic side component activity of the antiphlogistic Diclofenac.

Tables 2 and 3 show the results using different antiphlogistics. In each case here the dosage of Flupirtin was held constant and the dosage of antiphlogistic varied and in this manner in each case there was ascertained $ED_{50}$ of the analgetic side component of the antiphlogistic used.

In contrast when the Flupiritin is varied there is found in the same manner as stated in Table 1 also with the antiphlogistics of Table 2 the synergistic increase of the analgetic Flupirtin effect.

TABLE 2

Writhing Test According to Koster et al.: Fed. Proc. 18, 412 (1959)
Animal: White Mouse (NMRI-Mouse); Application: per os

| Active Material Combination | Active Material Dosage (mg/kg) per oral | Activity in % Average of 10 Mice | $ED_{50}$ mg/kg Determination 30 Minutes After Giving The Substance. Method of Linear Regression |
|---|---|---|---|
| Indometacin alone | | | Indometacin |
| | 2.0 | 17.3 | |
| | 4.0 | 50.0 | 4.3 |
| | 8.0 | 86.3 | |
| | 16.0 | 82.1 | |
| 2.24 mg/kg Flupirtin (Gluconate) + Indometacin | | | Indometecin in the Combination |
| | Indometacin | | |
| | 0.5 | 37.3 | |
| | 1.0 | 39.3 | |
| | 2.0 | 50.0 | 1.4 |
| | 4.0 | 68.0 | |
| | 8.0 | 84.7 | |
| Naproxen alone | | | Naproxen |
| | 0.38 | 21.7 | |
| | 0.75 | 42.0 | |
| | 1.5 | 43.4 | 2.62 |

TABLE 2-continued

Writhing Test According to Koster et al.: Fed. Proc. 18, 412 (1959)
Animal: White Mouse (NMRI-Mouse); Application: per os

| Active Material Combination | Active Material Dosage (mg/kg) per oral | Activity in % Average of 10 Mice | $ED_{50}$ mg/kg Determination 30 Minutes After Giving The Substance. Method of Linear Regression |
|---|---|---|---|
| | 3.0 | 53.8 | |
| | 6.0 | 70.0 | |
| | 12.0 | 74.1 | |
| | 24.0 | 54.5 | |
| 2.24 mg/kg Flupirtin (Gluconate) + Naproxen | | | Naproxen in the Combination |
| | Naproxen | | |
| | 0.10 | 40.1 | |
| | 0.19 | 55.0 | 0.17 |
| | 0.38 | 61.6 | |
| Piroxicam alone | | | Piroxicam |
| | 1.0 | 38.2 | |
| | 3.0 | 40.0 | 3.46 |
| | 4.0 | 53.6 | |
| | 5.0 | 61.8 | |
| | 10.0 | 70.9 | |
| | 20.0 | 49.1 | |
| 2.24 mg/kg Flupirtin (Gluconate) + Pirocixam | | | Piroxicam in the Combination |
| | Piroxicam | | |
| | 0.5 | 34.5 | |
| | 1.0 | 40.0 | |
| | 3.0 | 58.6 | 1.55 |
| | 4.0 | 64.1 | |
| | 5.0 | 72.4 | |
| | 10.0 | 80.0 | |
| Acetylsalicylic Acid Alone | | | Acetylsalicylic Acid |
| | 25.0 | 11.0 | |
| | 50.0 | 30.1 | 148.7 |
| | 75.0 | 39.0 | |
| | 100.0 | 41.1 | |
| | 150.0 | 43.2 | |
| | 200.0 | 59.6 | |
| | 400.0 | 71.2 | |
| 2.24 mg/kg Flupirtin (Gluconate) + Acetylsalicylic acid (ASS) | | | Acetylsalicylic Acid in the Combination |
| | ASS | | |
| | 12.50 | 39.4 | |
| | 25.0 | 41.8 | |
| | 50.0 | 55.8 | 31.20 |
| | 100.0 | 68.5 | |
| | 200.0 | 83.6 | |
| | 400.0 | 89.1 | |
| Sulindac alone | | | Sulindac |
| | 0.47 | 29.6 | |
| | 0.94 | 44.6 | |
| | 1.88 | 49.7 | |
| | 3.75 | 56.0 | 2.3 |
| | 7.50 | 61.0 | |
| | 15.00 | 71.1 | |
| | 30.00 | 72.3 | |
| 2.24 mg/kg Flupirtin (Hydrochloride) + Sulindac | | | Sulindac in the Combination |
| | Sulindac | | |
| | 0.06 | 39.5 | |
| | 0.12 | 44.6 | |
| | 0.24 | 58.0 | 0.15 |
| | 0.47 | 66.2 | |
| | 0.94 | 72.6 | |
| Isoxicam alone | | | Isoxicam |
| | 3.0 | 10.1 | |
| | 4.0 | 30.2 | |
| | 5.0 | 36.7 | |
| | 6.0 | 46.0 | 6.6 |
| | 7.0 | 51.1 | |
| | 8.0 | 62.6 | |
| | 10.0 | 66.2 | |
| 2.24 mg/kg Flupirtin (Hydrochloride) + Isoxicam | | | Isoxicam in the Combination |
| | Isoxicam | | |
| | 2.0 | 42.3 | |
| | 4.0 | 44.7 | |
| | 5.0 | 50.0 | 4.2 |
| | 6.0 | 52.0 | |
| | 7.0 | 54.0 | |

TABLE 2-continued

Writhing Test According to Koster et al.: Fed. Proc. 18, 412 (1959)
Animal: White Mouse (NMRI-Mouse); Application: per os

| Active Material Combination | Active Material Dosage (mg/kg) per oral | Activity in % Average of 10 Mice | $ED_{50}$ mg/kg Determination 30 Minutes After Giving The Substance. Method of Linear Regression |
|---|---|---|---|
| | 8.0 | 66.7 | |
| | 10.0 | 70.0 | |

TABLE 3

Randall-Selitto-Test According to Randall, Selitto, Arch. int.
Pharmacodyn. 111, page 409 (1957)
Animal: Albino-Rat (Sprague-Dawley); Application: per os

| Active Material Combination | Active Material Dosage (mg/kg) per oral | Activity in % Average of 6 Rats | $ED_{50}$ mg/kg Determination 30 Minutes After Giving the Substance. Method of Linear Regression |
|---|---|---|---|
| Flupirtin (Hydrochloride) alone | | | Flupirtin |
| | 10.0 | −8.3 | |
| | 20.0 | 23.2 | |
| | 30.0 | 45.8 | 30.94 |
| | 40.0 | 67.5 | |
| Diclofenac alone | | | Diclofenac |
| | 1.0 | 20.99 | |
| | 3.0 | 32.60 | |
| | 10.0 | 100.55 | 2.95 |
| | 30.0 | 135.36 | |
| 30.0 mg/kg Flupirtin (Hydrochloride) + Diclofenac | | | Diclofenac in the Combination |
| | Diclofenac | | |
| | 0.5 | 28.57 | |
| | 1.0 | 55.71 | 1.11 |
| | 3.0 | 63.33 | |
| | 10.0 | 107.14 | |
| Indometacin alone | | | Indometacin |
| | 1.0 | 12.3 | |
| | 2.0 | 22.05 | 2.77 |
| | 4.0 | 58.97 | |
| | 8.0 | 114.87 | |
| | 16.0 | 127.18 | |
| 30.0 mg/kg Flupirtin (Hydrochloride) + Indometacin | | | Indometacin in the Combination |
| | Indometacin | | |
| | 0.05 | 28.4 | |
| | 0.1 | 76.9 | 0.069 |
| | 1.0 | 91.12 | |

The lowest analgetically effective dosage in the Writhing Test on the mouse for example is with 2.24 mg/kg per os Flupirtin alone and 3.9 mg/kg per os Diclofenac alone. The lowest analgetically effective dosage in the Writhing test in the mouse for the combination for example is with 2.24 mg/kg per os Flupirtin and 0.49 mg/kg per os Diclofenac.

For example, there is found on the same animal models a clearly recognizable analgetic activity at the following dosages for the combination of:

2.24 mg/kg per os Flupirtin and 0.5 mg/kg per os Indometacin or 2.24 mg/kg per os Flupirtin and 0.2 mg/kg per os Naproxen or 2.24 mg/kg per os Flupirtin and 0.5 mg/kg per os Piroxicam or 2.24 mg/kg per os Flupirtin and 0.06 mg/kg per os Sulindac or 2.24 mg/kg per os Flupirtin and 2.0 mg/kg per os Isoxicam or 2.24 mg/kg per os Flupirtin and 12.5 mg/kg per os Acetylsalicylic acid.

As the general dosage range for the analgetic effect in the Writhing test on the mouse there is employed for example:

2.24 mg/kg per os Flupirtin and 0.49-15 mg/kg per os Diclofenac or 2.24 mg/kg per os Flupirtin and 0.5-8 mg/kg per os Indometacin or 2.24 mg/kg per os Flupirtin and 0.1-12 mg/kg per os Naproxen or 2.24 mg/kg per os Flupirtin and 0.5-10 mg/kg per os Piroxicam or 2.24 mg/kg per os Flupirtin and 0.06-0.94 mg/kg per os Sulindac or 2.24 mg/kg per os Flupirtin and 2.0-10 mg/kg per os Isoxicam or 2.24 mg/kg per os Flupirtin and 12.5-400 mg/kg per os Acetylsalicylic acid.

In the Writhing Test on the mouse the weight ratio of Flupirtin to the antiphlogistic Diclofenac can be for example:

1 part by weight Flupirtin to from 0.01 to 200 parts by weight antiphlogistic, preferably 1 part by weight Flupirtin to from 0.01 to 100 parts by weight antiphlogistic especially 1 part by weight Flupirtin to from 0.01 to 50 parts by weight antiphlogistic.

The parts by weight of Flupirtin to the antiphlogistic for the combination of the invention in the Writhing Test on the mouse can be for example:

Flupritin: Diclofenac from 1:0.01 to 1:7.0
Flupirtin: Indometacin from 1:0.06 to 1:3.57
Flupirtin: Naproxen from 1:0.17 to 1:5.36
Flupirtin: Piroxicam from 1:0.22 to 1:4.46
Flupirtin: Sulindac from 1:0.027 to 1:1.67
Flupirtin: Indometacin from 1:0.89 to 1:4.46
Flupirtin: Acetylsalicylic acid from 1:5.58 to 1:178.6

The total dosage for the combination in the animal tests for example is between 1 mg/kg and 300 mg/kg, preferably between 2 and 100 mg/kg, especially between 2 and 50 mg/kg per os. For example there is obtained for the synergistic analgetic effect of Flupirtin and antiphlogistic in the Writhing test on the mouse a 50% inhibition of pain at the following dosages:

9.0 mg/kg per os Flupirtin and 0.29 mg/kg per os Diclofenac or 2.24 mg/kg per os Flupirtin and 1.4 mg/kg per os Indometacin or 2.24 mg/kg per os Flupirtin and 0.17 mg/kg per os Naproxen or 2.24 mg/kg per os Flupirtin and 1.55 mg/kg per os Piroxicam or 2.24 mg/kg per os Flupirtin and 4.2 mg/kg per os Isoxicam or 2.24 mg/kg per os Flupirtin and 0.15 mg/kg per os Sulindac or 2.24 mg/kg per os Flupirtin and 31.2 mg/kg per os Acetylsalicylic acid In regard to the antiphlogistic effect for example with a combination of 30 mg/kg Flupirtin and 9 mg/kg per os Diclofenac the antiphlogistic effect of the Flupirtin is increased by around a factor of 2 and that of the Diclofenac at least around a factor of 2 (Adjuvans-Arthritis test, Carrageenin-Edema test, Bradykinin-Edema test on the rat; the synergistic increase in effect on the rat is especially marked if in the combination Flupirtin/Diclofenac there is present at least 30 mg Flupirtin). In this connection see the following table:

The combinations of the invention are indicated for example for treating the following conditions: inflammatory, degenerative articular, and extraarticular rheumatic diseases, Morbus Bechterew, non-rheumatic inflammations and swellings, non-rheumatic pain conditions, chronic polyarthritis, Arthosis deformans, soft part rheumatisms, postoperative pains, especially pains after throat, nose and ear operations, extraction of teeth and surgical operations in accidents; pains after trauma, especially after fractures, luxations and dislocations; pains with inflammatory conditions in the genital area, especially with endometritis, adnexitis and pelveoperitonitis; carcinoma pains, dysmenorrhea. Contraindications for example are: gastrointestinal difficulties, stomach and intestinal ulcers, greatly shrunken kidney and liver functions, asthma.

According to the invention there is dispensed, combination of Flupirtin and the antiphlogistic in a daily dosage of 100 to 1200 mg, preferably 100 to 800 mg, especially 100 to 600 mg or even 100 to 300 mg of Flupirtin and 1–1600 mg respectively 2–1200 mg or 5–1000 mg, preferably 10–600 mg, especially 15–300 mg of the antiphlogistic (with acetylsalicylic acid this daily dosage can even be up to 3000 mg). With carcinoma pains the amount of Flupirtin for example can be especially between 1000–1500 mg, preferably 1000–1200 mg. The daily dose can be employed in the form of a single dispensation of the total amount or in the form of 1 to 6, especially 1 to 4 partial doses per day. Generally there is preferred a dispensation 1 to 4 times, especially 1 to 3 times daily. The individual dosage of the combination of Flupirtin and the non-steroidal antiphlogistic in general contains 10 to 300 mg, preferably 15 to 200 mg, especially 25 to 150 mg of Flupirtin and 1 to 400 mg, preferably 1 to 350 mg, especially 1 to 300 mg of non-steroidal antiphlogistic, whereby these dosage units for example can be dispensed 1 to 6 times, especially 2 to 4 times daily.

It goes without saying that there can also be produced galenic preparations which contain the above stated dosage units 2 to for example 6 times. Thus for example tablets or capsules of the combination of the invention can be produced which contain 25–900 mg of

| Combination of Active Material | Dosage Active Material mg/kg per oral | Activity in % (− = inhibiting) 6 Rats | $ED_{50}$ mg/kg. Method of Linear Regression |
|---|---|---|---|
| Bradykinin-Edema-Test Relying On and Modification of the Method of Morsdorf et al (Arch. int. Pharmacodyn. 192,111-127 (1971). Animal: Albino-rat (Sprague-Dawley): | | | |
| Flupirtin (Hydrochloride) alone | | | Flupirtin no $ED_{50}$ Defineable |
| | 5.0 | +4.6 | |
| | 10.0 | −25.0 | |
| | 20.0 | −13.6 | |
| | 30.0 | −2.3 | |
| Diclofenac alone | | | Diclofenac No $ED_{50}$ Defineable |
| | 1.0 | +2.9 | |
| | 3.0 | +8.6 | |
| | 9.0 | −31.4 | |
| | 27.0 | −45.7 | |
| 30.0 mg/kg Flupirtin (Hydrochloride) + Diclofenac | | | Diclofenac in the Combination |
| | Diclofenac | | |
| | 1.0 | −16.4 | |
| | 3.0 | −32.8 | |
| | 9.0 | −67.2 | 4.8 | the Flupirtin component (with powders, granulates, solutions or suspensions for example 25-1800 mg of Flupirtin).

In the case of the non-steroidal antiphlogistics of the type "arylpropionic acids" the antiphlogistically active component dosage can also be 50-1500 mg a day. Generally there is valid in regard to the antiphlogistic components the known and previously proposed daily dosages. These types of dosages for example are the following:

| Non-Steroidal Antiphlogistic | Daily Dose | Individual Dose | Frequency of Application per day |
|---|---|---|---|
| Diclofenac | 100 mg | 50-100 mg | 1-3 times |
| Indometacin | up to maximal 200 mg | 25-100 mg | 1-6 times |
| Naproxen | 500-1000 mg | 250-500 mg | 2-4 times |
| Sulindac | 400 mg | 100 mg | 2 × daily 2 tablets |
| Isoxicam | 200-300 mg | 100-300 mg | 1 time |
| Acetylsalicylic Acid | up to maximal 5000 mg, especially 500 mg | 500-1000 mg | 1-8 times, especially 1-3 times |
| Piroxicam | up to maximal 40 mg especially 20 mg | 20 mg | 1 time |

For the combination of the Flupirtin and Diclofenac the daily dosage is generally 100-1500 mg, preferably 100-1200 mg, especially 100-800 mg of Flupirtin and 10-200 mg, especially 10-120 mg of Diclofenac 1 time daily. Especially this daily dosage amounts to about 100-1000 mg of Flupirtin and about 10-150 mg of Diclofenac once daily.

With several applications daily the mentioned dosages are apportioned correspondingly.

The dosage unit of the combination of Flupirtin and Diclofenac contains for example 10-300 mg, preferably 15-200 mg, especially 25-150 mg of Flupirtin and 3-50 mg, preferably 5-30 mg, especially 8-20 mg of Diclofenac, whereby this dosage unit can be dispensed 1-6 times daily. A favorable dosage unit for example contains about 100 mg of Flupirtin and about 25 mg of Diclofenac, which is dispensed for example 3 times daily.

In the following there are noted examples of the combination of Flupirtin with other antiphlogistics which state the amounts occurring in a dosage unit of each antiphlogistic, whereby for the Flupirtin in each case there are the ranges which for example are stated above for the combination with Diclofenac.

Indometacin (Amount of Indometacin in the Combination with Flupirtin per Dosage Unit):
5 to 100 mg, preferably 10 to 70 mg, especially 15 to 50 mg.

Naproxen (Amount of Naproxen in the Combination With Flupirtin per Dosage Unit):
25 to 250 mg, preferably 50 to 125 mg, especially 70 to 100 mg.

Sulindac (Amount of Sulindac in the Combination With Flupirtin per Dosage Unit):
2 to 100 mg, preferably 5 to 75 mg, especially 10 to 50 mg.

Isoxicam (Amount of Isoxicam in the Combination With Flupirtin per Dosage Unit):
10 to 150 mg, preferably 20 to 100 mg, especially 30 to 75 mg.

Piroxicam (Amount of Piroxicam in the Combination With Flupirtin per dosage Unit):
1 to 10 mg, preferably 1 to 7.5 mg, especially 2 to 5 mg.

Acetylsalicylic Acid (ASS) (Amount of Acetylsalicylic Acid in the Combination With Flupirtin per Dosage Unit):
100 to 1500 mg, preferably 200 to 1000 mg, especially 300 to 500 mg.

What has been previously said for example is also true in regard to these dosage units that it goes without saying that there can also be produced such galenic preparations which contain 2 to, for example, 6 times the stated dosage unit of active material.

Preferably the medicine is applied perorally. Flupirtin and each antiphlogistic can be used in each case as separate formulations or together in a galenical formulation. According to a preferred illustration of the invention the medicine can be formulated in the form of an individual dosage (that is in the form of a mixture) for peroral, parenteral (intravenous, intramuscular, subcutaneous), rectal, transdermal or vaginal dispensation, for example in the form of tablets, capsules, pills, dragees, granulates, suppositories, pellets, plaster, a solution, suspension or emulsion whereby the active materials are combined with corresponding adjuvants and carriers.

The non-steroidal antiphlogistic is present in the combination based on one part by weight of Flupirtin for example in the following ratio: 0.05 to 120, preferably 0.05 to 60 parts by weight. In the case of acetylsalicylic acid is not chosen, the combination contains for example per one part by weight Flupirtin 0.05 to 40, preferably 0.1 to 20 parts by weight antiphlogistic. Specially with the combination with acetylsalicylic acid the combination contains per one part by weight Flupirtin for example 10 to 120, preferably 15 to 60, especially 20 to 30 parts by weight acetylsalicylic acid.

In general, for the combination with the non-steroidal antiphlogistics of the type of the arylacetic acids or arylpropionic acids these are easily formulated to medicines for example, 0.1 to 25 mg of non-steroidal antiphlogistic and 5-150 mg Flupirtin, preferably 0.2-20 mg non-steroidal antiphlogistic and 10-100 mg Flupirtin, especially 0.5-15 mg non-steroidal antiphlogistic and 20-60 mg Flupirtin.

For the combination with the non- steroidal antiphlogistics of the Oxicam type there are for example formulated into medicines for example 0.1-20 mg non-steroidal antiphlogistic and 5-150 mg Flupirtin, preferably 0.2-15 mg non-steroidal antiphlogistic and 10-100 mg Flupirtin, especially 0.4-8 mg non-steroidal antiphlogistic and 20-60 mg Flupirtin.

The previously stated amounts by weight are valid, preferably for homogeneous mixtures of non-steroidal antiphlogistics and Flupirtin (for example, one layer tablets). Other amounts and ratios it should be understood are likewise possible, especially also with capsules or two layer tablets.

There can be produced tablets of different sizes, for example with a total weight of about 50-800 mg. They contain the active materials in the above-mentioned amounts and customary carriers and/or diluents and/or adjuvants. These tablets can also be provided for the dispensation of partial dosages. In corresponding manner for example, other preparations can also be formulated, such as for examples gelatin capsules or forms with sustained release.

Liquid medicinal preparations can be produced by dissolving or suspending the combination of active materials according to the invention in customary liquid carriers, whereby for example dosages are established which correspond to the amount of 1–3 teaspoons.

These types of formulations can be dispensed to the patients in 1–4 doses per day.

The individual dosages of the combination according to the invention for example can be:

(a) with peroral medicines:

Flupirtin: 10 to 300 mg, preferably 15 to 200 mg, especially 25 to 150 mg,

Antiphlogistic of Formula I: for example 1 to 400 mg, preferably 1 to 350 mg, especially 1 to 300 mg.

In a combination with acetylsalicylic acid the dosage unit contains for example 100 to 1500 mg, preferably 200 to 1000 mg, especially 300 to 500 mg acetylsalicylic acid.

In a combination with Oxicam the oral dosage unit contains for example 1 to 10 mg, preferably 1 to 7.5 mg, especially 2 to 5 mg of the Oxicam.

(These dosages can be dispensed for example 1–6, preferably 1–4, especially 1–3 times daily.)

(b) With parenteral medicines (for example intravenously, intramuscularly):

Flupirtin: 50 to 200 mg, preferably 50 to 150 mg, especially 100 to 120 mg,

Antiphlogistic of Formula I: for example 1 to 400 mg, preferably 1 to 350 mg, especially 1 to 300 mg.

In combination with acetylsalicylic acid the dosage unit contains for example 100 to 1500 mg, preferably 200 to 1000, especially 300 to 500 mg acetylsalicylic acid.

In a combination of Oxicames the parenteral dosage unit contains for example 1 to 10 mg, preferably 1 to 7.5 mg, especially 2 to 5 mg of the Oxicam.

(The dosages can be dispensed for example 1–6, preferably 1–4, especially 1–3 times daily.)

(c) with medicines for rectal or vaginal applications:

Flupirtin: 75 to 450 mg, preferably 100 to 350 mg, especially 150 to 300 mg,

Antiphlogistic of Formula I: for examples 1 to 400 mg, preferably 1 to 350 mg, especially 1 to 300 mg.

In a combination with acetylsalicylic acid the dosage unit contains for example 100 to 1500 mg, preferably 200 to 1000 mg, especially 300 to 500 of acetylsalicylic acid.

The oral dosage unit in a combination with an Oxicam contains for example 1 to 10 mg, preferably 1 to 7.5 mg, especially 2 to 5 mg of the Oxicam.

(These dosages can be dispensed for example 1–6, preferably 1–4, especially 1–3 times daily.)

(d) With medicines for application to the skin and mucous membranes (for example as solutions, lotions, emulsions, salves, plasters, etc.):

Flupirtin: 10 to 300 mg, preferably 15 to 200 mg, especially 25 to 150 mg,

Antiphlogistic of Formula I: for example 1 to 400 mg, preferably 1 to 350 mg, especially 1 to 300 mg.

In a combination with acetylsalicylic acid the dosage unit contains for example 100 to 1500 mg, preferably 200 to 1000 mg, especially 300 to 500 mg of acetylsalicylic acid.

In a combination with Oxicams such a dosage unit contains for example 1 to 10 mg, preferably 1 to 7.5 mg, especially 2 to 5 mg of the Oxicam.

(These dosages can be dispensed for example 1–6, preferably 1–4, especially 1–3 times daily.)

The range in amounts of the dosage units of Flupirtin and the amounts of the antiphlogistic set forth above are exchangeable for each other. Thus for example in the combination Flupirtin-Diclofenac the dosage unit contains 10–300 mg Flupirtin and 3–50 mg Diclofenac or 10–300 mg Flupirtin and 8–20 mg Diclofenac or 25–150 mg Flupirtin and 3–50 mg Diclofenac or 25 to 150 mg Flupirtin and 5–30 mg Diclofenac. It is obvious these ranges can be so correlated in relation to each other that in each case the largest general range of Flupirtin is related to the largest general range of the antiphlogistic (for example a combination of 10–300 mg Flupirtin and 3–50 mg Diclofenac), the preferred range of Flupirtin to the preferred range of each antiphlogistic and the "especial range" of Flupirtin to the "especial range" of each antiphlogistic.

The dosages stated above and the parts by weight, which refer to use by humans, in each case are based on the free bases respectively, free acids.

The acute toxicity of the combinations of the invention on the mouse (expressed by the $LD_{50}$ mg/kg; method: Litchfield and Wilcoxon, J. Pharmacol. Exper. Ther. Vol. 95, page 99 (1949) is for example for the combination Flupirtin (maleate) and Diclofenac (1:1) in oral application 504 mg/kg respectively above 471 mg/kg body weight. The $LD_{50}$ of Diclofenac alone for example is considerably lower, namely 172 mg/kg. On the same experimental animal species further examples are mentioned here.

For the combination of Flupirtin (maleate) and Indometacin (1:1) in oral application the $LD_{50}$ is 633 mg/kg body weight respectively above 577 mg/kg body weight. ($LD_{50}$ of Indometacin alone: 21 mg/kg). For the combination of Flupirtin (maleate) and Naproxen (1:1) in oral application the $LD_{50}$ is at 613 mg/kg body weight respectively above 605 mg/kg body weight.

For the combination of Flupirtin (maleate) and Piroxicam (1:1) in oral application the $LD_{50}$ is at 793 mg/kg body weight respectively above 731 mg/kg body weight ($LD_{50}$ of Piroxicam alone: 350 mg/kg). For the combination of Flupirtin (maleate) and Sulindac (1:1) in oral application the $LD_{50}$ is at 550 mg/kg body weight or above 505 mg/kg body weight ($LD_{50}$ of Sulindac alone: 507 mg/kg). For the combination of Flupirtin (maleate) and acetylsalicylic acid (ASS) (1:13.9) in oral application the $LD_{50}$ is at 1942 mg/kg, based on Flupirtin, respectively at 1679 mg/kg body weight, based on ASS ($LD_{50}$ of ASS alone: 815 mg/kg).

For the combination of Flupirtin (maleate) and Isoxicam (1:1) in oral application the $LD_{50}$ is at 727 mg/kg body weight respectively above 686 mg/kg body weight.

Hereby of especial significance is the fact that the gastrointestinal side effect action with the combination according to the invention of Flupirtin with the non-steroidal antiphlogistics is surprisingly reduced. Thus for example on the albino rat (Sprague-Dawley) there was not established any ulcerogenic effect (stomach mucosa erosion) on the stomach 24 hours after application of a single dispensation per os of the combination of 30 mg/kg Flupirtin and 24 mg/kg Diclofenac, while after a single dispensation of 24 mg/kg Diclofenac alone (per os) after 24 hours there occurred with the animals erosion of the stomach mucosa. Likewise on the same animal models for example after a single dispensation of the combination of 30 mg/kg per os Flupirtin and 0.1 mg/kg per os Indometacin there was not formed any stomach ulcers within 24 hours.

It can be seen from the following table that for example frequently the $LD_{50}$ of the non-steroidal antiphlogistic is increased through the combination of the invention, that is the tolerance of the antiphlogistic is also increased by the combination of the invention. This is especially so for those antiphlogistics which have a low $LD_{50}$ that is are of low tolerance, as for example Indometacin, Diclofenac.

$LD_{50}$ Values for the Non-Steroidal Antiphologistic in the Combination. Animal: NMRI-Mouse, Application: per os, Method: Litchfield; J. T., Wilcoxon, F.; J. Pharmacol. Exper. Ther. 95:99, 1949

| Active Material Combination Ratio of Flupirtin (Maleate) to the Antiphlogistic (Parts by Weight) | $LD_{50}$ Values of the Non-Steroidal Antiphologistic in the Combination |
|---|---|
| Diclofenac, alone | 172 mg/kg (Arzneim. Forsch. 33, 1555, 83) |
| Flupirtin (Maleate) + Diclofenac 1:1 | 252 mg/kg |
| Flupirtin (Maleate) + Diclofenac 1:0.82 | 258 mg/kg |
| Indometacin, alone | 21 mg/kg (Arzneim. Forsch. 33, 1555, 83) |
| Flupirtin (Maleate) + Indometacin 1:1 | 316 mg/kg |
| Flupirtin (Maleate) + Indometacin 1:0.63 | 242 mg/kg |
| Piroxicam, alone | 350 mg/kg (Basic Pharmacology and Therapeutics 8,4639,80) |
| Flupirtin (Maleate) + Piroxicam 1:1 | 396 mg/kg |
| Acetylsalicylic acid, alone | 815 mg/kg (Toxicology and Applied Pharmacology 23, 537, 72) |
| Flupirtin (Maleate) + Acetylsalicylic acid 1:13.93 | 1811 mg/kg |

The composition according to the invention are suitable for the production of pharmaceutical compositions and preparations. The pharmaceutical compositions or medicaments contain, as active principle Flupirtin as well as the non-steroidal antiphlogistics, in a given case, in admixture with other pharmacologically or pharmaceutically active substances. The medicaments may be prepared in known manner with the usual pharmaceutical excipients, assistants, carriers, and diluents.

As carriers and adjuvants, for example, are those recommended in the following literature as adjuvants for pharmacy, cosmetic, and related fields such as Ullmann's Encyklopädie der technischern Chemie, Volume 4 (1953), pages 1–39, Journal of Pharmaceutical Sciences 52 (1963), pages 918 et seq; H. V. Czetsch-Lindenwald, Hilfsstoffe fur Pharmazie und angrenzende Gebiete; Pharm Ind. 2 (1961), pages 72 et. seq.; Dr. H. P. Fiedler, Lexikon der Hilfsstoffe fur Pharmazie, Kosmetik und angrenzende Gebiete, 2nd edition, Editio Cantor, Aulendorf i. Wurtt (1981).

Examples of such materials include gelatin, natural sugars such as sucrose or lactose, lecithin, pectin, starch (for example, cornstarch, cyclodextrin and cylcodextrin derivatives as well as starch derivatives), polyvinyl-pyrrolidone, gelatins, cellulose derivatives (for example cellulose ethers in which the cellulose hydroxy groups are partially etherified with lower saturated aliphatic alcohols and/or lower saturated hydroxy-alcohols (for example methyl cellulose, hydroxypropylmethyl cellulose)), stearates, e.g. methylstearate and glycerol stearate, magnesium and calcium salts of fatty acids with 2 to 22 (especially 10 to 18) carbon atoms, especially saturated acids (for example, calcium stearate, calcium laurate, magnesium oleate, calcium palmitate, calcium behenate and magnesium stearate), emulsifiers, oils and fats (castor oil, olive oil, sesame oil, cottonseed oil, corn oil, wheat germ oil, sunflower seed oil, cod-liver oil), mono-di and triglycerides of saturated fatty acids $C_{12}H_{24}O_2$ to $C_{18}H_{38}O_2$ and their mixtures (e.g. glyceryl monostearate, glyceryl distearate, glyceryl tristearate, glyceryl trilaurate), pharmaceutically compatible mono- or polyvalent alcohols and polyglycols such as glycerine, mannitol, sorbitol, pentaerythritol, ethyl alcohol, diethylene glycol, triethyl glycol, propylene glycol, dipropylene glycol, as well as derivatives of such alcohols and polyglycols, esters of saturated and unsaturated fatty acids 2 to 22 carbon atoms, especially 10 to 18 carbon atoms), with monohydric aliphatic alcohols (1 to 20 carbon atom alkanols) or polyhydric alcohols such as glycols, glycerine, diethylene glycol, pentaerylthritol, sorbitol, mannitol, ethyl alcohol, butyl alcohol, octadecyl alcohol, etc. e.g. glyceryl stearate, glyceryl palmitate, glycol distearate, glycol dilaurate, glycol diacetate, monoacetin, triacetin, glyceryl oleate, ethylene glycol stearate, such esters of polyvalent alcohols can in a given case also be etherified, benzyl benzoate, dioxolane, glycerine formal, tetrahydrofurfuryl alcohols, polyglycol ethers with 1 to 12 carbons atom alcohol, dimethyl acetamide, lactamide, lactates, e.g. ethyl lactate, ethyl carbonate, silicones (especially middle viscosity dimethyl polysiloxane), calcium carbonate, sodium carbonate, sodium phosphate.

As further adjuvants there can be used materials which cause disintegration (so-called disintegrants) such as: cross-linked polyvinyl pyrrolidone, sodium carboxymethyl-starch, sodium carboxymethyl cellulose or microcrystalline cellulose. Likewise there can be used jacketing materials such as for example: polyacrylic acid esters, cellulose ethers and the like.

For the production of solutions there can be used water or physiologically compatible organic solvents, as for example, ethanol, 1,2-propylene glycol, polyglycols, e.g. diethylene glycol, triethyl glycol, and dipropylene glycol and their derivatives, dimethyl sulfoxide, fatty alcohols, e.g. stearyl alcohols, cetyl alcohol, lauryl alcohol and oleyl alcohol, triglycerides, e.g. glyceryl oleate, glyceryl stearate, glyceryl palmitate, and glyceryl acetate, partial esters of glycerine, e.g. monoacetin, diacetin, glyceryl monostearate, glyceryl distearate, glyceryl monopalmitate, paraffins and the like.

For injectable solutions or suspensions there can be used non-toxic parenteral compatible diluents or solvents such as for example, water, 1,3-butanediol, ethanol, 1,2-propylene glycol, polyglycols mixed with water, Ringer's solution, isotonic salt solution or even hardened oils including synthetic mono or diglycerides or fatty acids such as oleic acid.

In the production of the preparation there can be used known and customary solution aids or emulsifiers. As solution aids and emulsifiers there can be used, for example, polyvinyl pyrrolidone, sorbitan fatty acids esters such as sorbitan trioleate, phosphatides such as lecithin, gum acacia, gum tragacanth, polyoxyethylated sorbitan monooleate, polyoxyethylated fats, polyoxyethylated oletriglycerides, linolized oleotriglycerides, polyethylene oxide-condensation products of fatty alcohols, alkylphenols or fatty acids or even 1-methyl-3-(2-hydroxyethyl)-imidazolidone-2. As used herein polyoxyethylated means that the materials in question contain polyoxyethylene chains whose degree of polymerization generally is between 2 and 40, particularly between 10 and 20.

Such polyoxyethylated materials for example can be obtained by reaction of hydroxyl group containing compounds (for example, mono- or diglycerides) or unsaturated compounds such as, for example, those containing the oleic acid radical with ethylene oxide (for example, 40 moles of ethylene oxide per mole of glycerides).

Examples of oleotriglycerides are olive oil, peanut oil, castor oil, sesame oil, cottonseed oil, corn oil (see also Dr. H. P. Fiedler, supra, pages 338–345).

Furthemore, there can be added preservatives, stabilizers, buffers, for example, calcium hydrogen phosphate, colloidal aluminum hydroxide, taste correctives, antioxidants and complex formers (for example, ethylene diamine tetraacetic acid) and the like. In a given case for stabilization of the active molecule the pH is adjusted to about 3 to 7 with physiologically compatible acids or buffers. Generally, there is preferred as neutral as possible to weak acid (to pH 5) pH value.

As antioxidants there can be used for example sodium meta bisulfite, ascorbic acid, gallic acid, butyl hydroxyanisole, nordihydroguajaretic acid, tocopherols, as well as tocopherol and synergists (materials which bind heavy metals by complex formation, for example, lecithin, ascorbic acid, phosphoric acid). The addition of synergists increases considerably the antioxidant activity of tocopherol. As preservatives there can be used for example sorbic acid, p-hydroxy-benzoic acid esters (for example, lower alkyl esters such as the methyl ester and the ethyl ester), benzoic acid, sodium benzoate, trichloroisobutyl alcohol, phenol, cresol, benzethonium chloride, and formalin derivatives.

The pharmaceutical and galenical treatment of the compounds of the invention takes place according to the usual standard methods. For example, the active material or materials and assistants or carriers are well mixed by stirring or homogenization (for example, by means of a colloid mill or ball mill or other customary mixing apparatus) wherein the operation is generally carried out at temperatures between 20° C. and 80° C., preferably 20° C. to 50° C. especially at room temperature. For the rest reference is made to the following standard work:

Sucker, Fuchs, Speiser, Pharmazeutische Technologie, Thieme-Verlag, Stuttgart, 1978. Short Description of the Pharmacological Test Methods Mentioned in the Application Randall-Selitto-Test (Inflammation Pain on the Rat)

In accordance with the method of Randall and Selitto (L. O. Randall, J. J. Selitto, Arch. int. Pharmacodyn., Volume 111, pages 409–418, 1957) rats were injected subplantarly with 1 ml of a 20% (in dimineralized water) brewer's yeast suspension in the right hind paw. 2½ hours later the test materials were dispensed and 30 minutes later the swelling pain measured with an Algesiemeter as pressure (in grams) on the inflamed paw (apparatus of Ugo Basile, Milan, Italy). As criteria there are considered the defensive reaction of the animals drawing the paw away and/or freeing themselves from the grip of the experimenters. The effect of the material was determined from the increase of the swelling pain compared to the untreated control group. The experimental procedure different from the original method in that the materials were applied 2½ hours after the setting of edema and not simultaneously therewith. In this way there should be prevented the development of edema, being checked by a possible antiphlogistic action and the analgesy superimposed or simulated.

The $ED_{50}$ was determined by means of the method of linear regression. The $ED_{50}$ is the dosage in mg/kg in which there is calculated a 50% analgetic action.

Acetic Acid-Test (Writhing Test) on the Mouse

Method:

In the acetic acid test according to Koster et al (Fed. Proc., Volume 18 (1959), page 412) the irritating pain was caused by an intraperitoneal injection of 1% acetic acid. The pain reaction is expressed as a characteristic stretching of the animals ("writhing syndrome") which persists in irregular time intervals for a long period of time after the injection of the acetic acid. The dosage dependent suppression of the frequency of the stretching motion compared to an untreated control group is expressed in percent as analgetic effect. The evaluation is carried out by determination of the $ED_{50}$ (Method of Linear Regression). The $ED_{50}$ is the dosage in mg/kg present at which mathematically a 50% suppression of the "writhing syndrome" is present.

The acetic acid test is marked by the fact that not only is there detectable the effect of strong, central acting analgetics but also preponderantly peripherally acting analgetics-antipyretics and antiphlogistically active pharmaceuticals such as phenyl butazone, Indometacin and others. Therewith the effect in this procedure refers to a peripheral component of the analgesic.

Hot Plate Test

Relying on the method of Janssen (P. A. J. Janssen and A. H. Jageneau, J. Pharm. Pharmacol., Volume 9 (1957), pages 318–400) mice were placed on a 55.5° C. hot plate. There was evaluated the reaction time until "licking" of the paws. The analgetic action of the materials is expressed in percent as the lengthening of the reaction time (in seconds) compared to a control group treated only with the vehicle.

The $ED_{50}$ is the dosage in mg/kg a 50% analgetic effect is present.

Carrageenin Edema Test on Antiphlogistic Activity

Relying on the modification of the method of Morsdorf et al (Arch. int. Pharmacodyn. Volume 192, pages 111–127 (1971)) male rats received subplantarly in the right hind paw an injection of a 1% carrageenin solution (Carrageenin, Type IV, Sigma C-3889). One hour and four hours later there was determined the volume of the paw. To measure the volume there was used a volume meter (Rhema-Labortechnik Company, D-6238 Hofheim, Type 2060). Directly after the first measurement the test substance was dispensed by means of a gullet stomach catheter. There was calculated the increase in the swelling of the paw in the second measurement compared to the first measurement in absolute values (ml). The evaluation included the determination of the percent average value of the difference of the edema volumes one and four hours after receiving the inflammatory solution. The edema inhibiting action was calculated in percent from the edema volume measured by water displacement in comparison to the edema volume of the untreated inflamed control group.

As $ED_{50}$ there is valid the dosage in mg/kg in which there is calculated a 50% inhibition of edema.

Bradykinin-Edema Test in Regard To Antiphlogistic Action

As the single change in comparison to the Carrageenin-Edema Test in place of Carrageenin there was injected subplantarly Bradykinin (Sigma B 3259) 0.01 mg/animal in 0.1 ml of a 0.9% sodium chloride solution.

Adjuvant Arthritis Test on the Rat On Antiphlogistic Effect

Relying on Newbould (Brit. J. Pharmacol., Volume 21 (1963), pages 127-136) there was induced the Adjuvant Arthritis by *Mycobacterium butyricum* by injecting the microorganism subplantarally in the right hind paw of the rat. The killed *Mycobacterial butyrica* were deposited in Freund's adjuvant (liquid paraffin) for the injection.

Hereby there was shown in the control (animals which did not receive test materials) already after 24 hours a measurable edema on the injected paw which remained almost of unchanged size for about 10 to 12 days (acute phase of the arthritis). Then there set in on the injected paw a further increase in volume of the edema (secondary phase of the arthritis=chronic inflammation), mixed with the residual of the acute inflammation of the first 10 days. Simultaneously with this second outburst on the injected paw there also occurred an edema on the paw not injected with the bacterium (chronic immunological inflammation).

The animals on which the test material were tested by prophylactic application received the test material 2 days before triggering the inflammation and the animals, on which test materials were treated in therapeutic application, 8 days after triggering the inflammation received a daily dose per os of the test material (that is, the combination Flupirtin+antiphlogistic, for example in the ratio 10 parts by weight Flupirtin to 1 or 3 parts by weight antiphlogistic). Then on the third or ninth day (according to the purpose of the test: prophylaxis or therapy) arthritis was caused by injection whereby the test materials were further dispensed in the same manner once daily per os during the entire duration of the test. The combination Flupirtin-antiphlogistic was dispensed in methyl cellulose mucilage. The total duration with prophylactic application of the test materials was 14 days and with therapeutic application 35 days. The antiphlogistic effect was calculated in percent from the edema volume measured by water displacement in comparison to the edema volume of the untreated control group as well as by determination of the maximum sizes of all differences to day 0.

Determination of the Maximum Sizes of All Differences to Day 0 is Explained as Follows:

In the test period of time once daily with the individual animals there was measured the swelling of the paw (that is the paw volume) by dipping the paw in water and determining the difference in each case to the paw volume at day 0. From this there results directly the maximum volume of the swelling during the test. Then there is calculated the average value of the maximum swelling and the applicable standard deviation.

Parallel as standard preparation there was cotested Indometacin. The evaluation was carried out by determination of the $ED_{50}$ (dosage, which produces 50% suppression of the volume increase of the edema) according to the method of linear regression.

Testing of Ulcerogenic Effect Relying On the Method of Jahn and Adrian (Arzneimittelforschung, Volume 19 (1969) pages 36-52)

The experimental animals are male albino rats which are maintained under the usual conditions at 21°-22° C. After 48 hours of qualified feeding the test materials were dispensed perorally an increasing dosages. The animals were killed 24 hours later and the stomachs investigated for ulcerogenic changes according to the method of Munchow, Arzneimittelforschung, Volume 4 (1954), pages 341-344. (The size of the ulcers formed is measured are classified according to Munchow.)

The composition can comprise, consist essentially of or consist of the stated materials and the process can comprise, consist essentially of or consist of the recited steps with such materials.

The composition can be used in human or veterinary medicine, e.g. to treat dogs, cats, cattle, sheep, and horses.

Unless otherwise indicated all parts and percentages are by weight.

DETAILED DESCRIPTION

EXAMPLE 1

Capsules Containing 150 mg Flupirtin Maleate and 20 mg Diclofenac-Sodium 300 grams of Flupirtin maleate were mixed with 40 grams of Diclofenac-sodium and subsequently granulated with a solution of 8 grams Kollidon VA64 (BASF) (Kollodian VA64 is a vinylpyrrolidone-vinyl acetate copolymer 60:40) in 300 ml of water. The dried granulate was passed through a sieve having a 1 mm mesh size and subsequently mixed with 1 gram of magnesium stearate and 1 gram of highly dispersed silica (Aerosil 200/Degussa).

The mixture in each case in an amount of 175 mg was filled into hard gelatin capsules of size 1.

On capsule contains 150 mg Flupirtin maleate and 20 mg Diclofenac-sodium.

In an analogous manner there can be produced capsules containing 100 mg Flupirtin maleate and 25 mg Diclofenac-sodium.

EXAMPLE 2

Tablets Containing 150 mg Flupirtin Maleate and 20 mg Diclofenac-Sodium 300 grams of Flupirtin maleate were mixed with 40 grams of Diclofenac-sodium and the mixture granulated with a mucilage made of 20 grams of cornstarch in 370 grams of water in customary manner. After drying the granulate was passed through a sieve having a mesh size of 0.8 mm and subsequently mixed with 300 grams of microcrystalline cellulose, 52 grams of modified starch (Starch 1500/Colorcon), 7 grams of magnesium stearate as well as 1 gram of highly dispersed silica (Aerosil 200/Degussa). (The modified starch was a free flowing and partially cold water soluble corn starch; this modification was carried out by purely physical procedures.) The mixture was pressed to oblong tablets having a weight of 360 mg, a length of 16 mm and a width of 7 mm.

Subsequently the tablets can in a given case be provided in the customary manner with a gastric juice resistant or gastric juice permeable or soluble film coating.

One tablet contains 150 mg of Flupirtin maleate as well as 20 mg of Diclofenac-sodium.

EXAMPLE 3

Capsules Containing 40 mg or 20 mg Flupirtin Maleate and 10 mg or 5 mg Diclofenac-Sodium 80 grams of Flupirtin maleate were mixed with 20 grams of Diclofenac-sodium and 150 grams of calcium hydrogen phosphate and subsequently granulated in the customary manner with a solution of 3 grams of Kollidon VA64 (BASF) in 115 ml of water. The dried granulate was passed through a sieve having a mesh size of 0.8 mm and subsequently mixed with 4 grams of magnesium stearate, 1 gram of highly dispersed silica and 42 grams of modified starch (Starch 1500/Colorcon).

The mixture was filled in each case in an amount of 150 mg into hard gelatin capsules of size 3.

One capsule contains 40 mg of Flupirtin maleate and 10 mg of Diclofenac-sodium.

In a similar manner there can be produced capsules having 20 mg Flupirtin maleate and 5 mg Diclofenac Sodium by granulating a mixture of 40 grams of Flupirtin maleate, 10 grams Diclofenac-sodium and 200 grams of calcium hydrogen phosphate with a solution of 3 grams of Kollidon VA64 (BASF) in 75 ml of water and further processing in the stated manner.

EXAMPLE 4

Tablets Containing 40 mg Or 20 mg Flupirtin Maleate and 10 mg Or 5 mg Diclofenac-Sodium 280 grams of Flupirtin maleate were mixed with 70 grams of Diclofenac-sodium and the mixture granulated in the customary manner with a mucilage made of 21 grams of corn starch in 400 grams of water. After drying the granulate was passed through a sieve having a mesh size of 0.8 mm and subsequently mixed with 280 grams of microcrystalline cellulose, 40.6 grams of modified starch (Starch 1500/Colorcon), 1.4 grams of highly dispersed silica and 7 grams of magnesium stearate. The mixture was pressed to biconvex tablets weighing 100 mg and having a diameter of 6 mm and a radius of curvature of 4 mm.

Subsequently the tablets in a given case, can be provided with a gastric juice resistant or gastric juice permeable or soluble film coating.

One tablet contains 40 mg of Flupirtin maleate and 10 mg of Diclofenac-sodium.

In a similar manner tablets containing 20 mg of Flupirtin maleate and 5 mg of Diclofenac-sodium can be produced by mixing 140 grams of Flupirtin maleate with 35 grams of Diclofenac-sodium and 175 grams of calcium hydrogen phosphate and the mixture granulated with a mucilage made of 21 grams of corn starch in 280 grams of water and, after drying further processed in the manner stated above.

EXAMPLE 5

Suppositories Containing 150 mg Flupirtin Maleate and 20 mg Diclofenac-Sodium 75 grams of Flupirtin maleate and 10 grams of Diclofenac-sodium were suspended in 950 grams melted hard fat (see Europaisches Arzneibuch, Volume III). (Hard fat is a mixture of mono-, di- and triglycerides of saturated fatty acids of the formula $C_{10}H_{20}O_2$ to $C_{18}H_{36}O_2$, decanoic acid to stearic acid.) After homogenization the suspension was poured into 2.3 ml hollow cells in customary manner and cooled.

A suppository weighing 2.07 grams contains 150 mg of Flupirtin maleate and 20 mg of Diclofenac-sodium.

In an analogous manner suppositories can be produced containing 150 mg Flupirtin maleate and 25 mg Diclofenac-sodium (the amount of melted hard fat is then reduced correspondingly).

EXAMPLE 6

Suppositories Containing 40 mg or 20 mg Flupirtin Maleate and 10 mg or 5 mg Diclofenac-Sodium 20 grams of Flupirtin maleate and 5 grams of Diclofenac-sodium were suspended in 995 grams of molten hard fat. After homogenization the suspension was poured into 2.3 ml hollow cells in customary manner and cooled.

A suppository weighing 2.04 grams contains 40 mg of Flupirtin maleate and 10 mg of Diclofenac-sodium.

In a similar manner suppositories containing 20 mg of Flupirtin maleate and 5 mg of Diclofenac-sodium can be prepared by employing 2015 grams of molten hard fat in place of the 995 grams of hard fat, otherwise the procedure was the same.

EXAMPLE 7

Capsules Containing 40 mg or 20 mg Flupirtin Maleate and 6 mg or 3 mg Piroxicam 80 grams of Flupirtin maleate were mixed with 12 grams of Piroxicam and 158 grams of calcium hydrogen phosphate and the mixture granulated with a solution of 3 grams of Kollidon VA64 (BASF) in 120 ml of water in customary manner. The dried granulate was passed through an 0.8 mm mesh sieve and subsequently mixed with 4 grams of magnesium stearate, 1 gram of highly dispersed silica and 42 grams of modified starch (Starch 1500/Colorcon).

The mixture in each case in an amount of 150 mg was fitted into size 3 hard gelatin capsules.

One capsule contains 40 mg of Flupirtin maleate and 6 mg of Piroxicam.

In similar manner capsules can be produced containing 20 mg of Flupirtin maleate and 3 mg of Piroxicam by mixing 40 grams of Flupirtin maleate and 6 grams of Piroxicam and 204 grams of calcium hydrogen phosphate, granulating the mixture with a solution of 3 grams of Kollidon VA64 (BASF) in 75 ml of water and after drying further processing the granulate in the manner stated above.

EXAMPLE 8

Suppositories Containing 40 mg or 20 mg Flupirtin Maleate and 6 mg or 3 mg Piroxicam 20 grams of Flupirtin maleate and 3 grams of Piroxicam were suspended in 997 grams of molten hard fat. After homogenization the suspension was poured into 2.3 ml hollow cells in customary manner and cooled.

A suppository weighing 2.04 grams contains 40 mg of Flupirtin maleate and 6 mg of Piroxicam.

In similar manner suppositories containing 20 mg of Flupirtin maleate and 3 mg of Piroxicam can be produced by employing 2017 grams of hard fat in place of 997 grams of hard fat, otherwise the procedure is the same.

The entire disclosure of German priority application No. P 3502005.9 is hereby incorporated by reference.

What is claimed is:

1. A medicine comprising a synergistic combination of
   (a) a member of the group consisting of Flupirtin and physiologically acceptable salt thereof, and
   (b) a non-steroidal (antiphlogistic selected from the group consisting of arylacetic acid and arylpropionic acid in which the aryl group in said arylacetic acid and aryl propionic acid is in the alpha position of said acid and is selected from the group consisting of phenyl and naphthyl, and physiologically acceptable salt thereof
   there being one part of member (a) for each 0.5 to 120 parts of the non-steroidal antiphlogistic (b).

2. A medicine according to claim 1 wherein the non-steroidal antiphlogistic is selected from the group consisting of Diclofenac and Naproxen.

3. A medicine according to claim 1 containing 0.05 to 60 parts by weight of the non-steroidal antiphlogistic.

4. A medicine according to claim 1 wherein the non-steroidal antiphlogistic is selected from the group consisting of Diclofenac, Naproxen and Sulindac.

5. A medicine according to claim 2 wherein the non-steroidal antiphlogistic is Diclofenac.

6. A medicine according to claim 1 in the form of a dosage unit containing 10 to 1800 mg of Flupirtin and 1 to 1600 mg of the antiphlogistic.

7. A medicine according to claim 6 wherein the non-steroidal antiphlogistic is selected from the group consisting of Diclofenac and Naproxen.

8. A medicine according to claim 7 wherein the non-steroidal antiphlogistic is Diclofenac.

9. A medicine according to claim 6 containing 15 to 1500 mg of Flupirtin and 1 to 1600 mg of the antiphlogistic.

10. A medicine according to claim 6 containing 10 to 1200 mg of Flupirtin and 2 to 500 mg of the antiphlogistic.

11. A medicine according to claim 10 containing 15 to 900 mg of Flupirtin.

12. A medicine according to claim 10 containing 50 to 600 mg of Flupirtin and 5 to 300 mg of the antiphlogistic.

13. A medicine according to claim 12 containing 50–400 mg of Flupirtin.

14. A medicine according to claim 13 wherein the non-steroidal antiphlogistic is selected from the group consisting of Diclofenac and Naproxen.

15. A medicine according to claim 14 wherein the non-steroidal antiphlogistic is Diclofenac.

16. A process in administering to a mammal in need thereof of a material having analgetic and antiphlogistic action comprising administering to said mammal the medicine of claim 1 in an amount effective to act synergistically as an analgetic and antiphologistic.

17. A process of administering to a mammal in need thereof of a material having analgetic and antiphlogistic action comprising administering to said mammal the medicine of claim 1 in an amount effective to act synergistically as an analgetic and antiphlogistic.

18. A process according to claim 16 wherein the non-steroidal antiphlogistic is selected from the group consisting of Diclofenac and Naproxen.

* * * * *